(12) United States Patent
Mihalef et al.

(10) Patent No.: US 9,462,954 B2
(45) Date of Patent: Oct. 11, 2016

(54) METHOD AND SYSTEM FOR BLOOD FLOW VELOCITY RECONSTRUCTION FROM MEDICAL IMAGES

(71) Applicant: Siemens Aktiengesellschaft, Munich (DE)

(72) Inventors: Viorel Mihalef, North Brunswick, NJ (US); Saikiran Rapaka, Ewing, NJ (US); Ali Kamen, Skillman, NJ (US); Puneet Sharma, Monmouth Junction, NJ (US)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 112 days.

(21) Appl. No.: 14/476,814

(22) Filed: Sep. 4, 2014

(65) Prior Publication Data

US 2015/0063649 A1 Mar. 5, 2015

Related U.S. Application Data (60) Provisional application No. 61/873,404, filed on Sep. 4, 2013.

(51) Int. Cl.
*A61B 5/026* (2006.01)
*G06T 7/20* (2006.01)
*A61B 5/055* (2006.01)

(52) U.S. Cl.
CPC .......... *A61B 5/026* (2013.01); *G06T 7/20* (2013.01); *A61B 5/055* (2013.01); *A61B 2576/00* (2013.01); *G06T 2207/10072* (2013.01); *G06T 2207/30048* (2013.01); *G06T 2207/30104* (2013.01)

(58) Field of Classification Search
None
See application file for complete search history.

(56) References Cited

U.S. PATENT DOCUMENTS

| 6,393,313 | B1 | 5/2002 | Foo | |
|---|---|---|---|---|
| 6,549,801 | B1 | 4/2003 | Chen et al. | |
| 7,270,635 | B2 * | 9/2007 | Pedrizzetti | G01F 1/663 600/454 |
| 8,483,466 | B2 | 7/2013 | Abe et al. | |
| 2008/0287799 | A1 * | 11/2008 | Hall | A61B 8/06 600/454 |
| 2010/0121204 | A1 * | 5/2010 | Utsuno | A61B 5/02007 600/485 |

(Continued)

OTHER PUBLICATIONS

Köhler, Benjamin, et al. "A Survey of Cardiac 4D PC-MRI Data Processing." (2015).*

(Continued)

*Primary Examiner* — Bhavesh Mehta
*Assistant Examiner* — Narek Zohrabyan (57) ABSTRACT

A method and system for blood flow velocity reconstruction from medical image data is disclosed. Flow system geometry of a flow conduit is generated from medical image data. The flow system velocity includes an inlet, walls, and one or more outlets of the flow conduit. A measured velocity field is extracted from the medical image data. Inlet and wall fluxes are estimated based on the measured velocity field or other external measurements. Outlet fluxes are estimated such that mass conservation is constrained based on the inlet and wall fluxes. A reconstructed velocity field is calculated by solving flux-constrained Poisson (FCP) equations that are constrained by the estimated output fluxes.

39 Claims, 5 Drawing Sheets

(56) References Cited

U.S. PATENT DOCUMENTS

| | | | |
|---|---|---|---|
| 2011/0064294 A1 | 3/2011 | Abe et al. | |
| 2011/0319775 A1* | 12/2011 | Fujii | A61B 3/1233 600/504 |
| 2012/0022843 A1* | 1/2012 | Ionasec | G06T 13/20 703/9 |
| 2012/0237104 A1* | 9/2012 | Fouras | A61B 5/08 382/132 |
| 2012/0265075 A1* | 10/2012 | Pedrizzetti | A61B 8/06 600/454 |
| 2013/0070062 A1 | 3/2013 | Fouras et al. | |
| 2013/0088227 A1* | 4/2013 | Wernik | A61B 5/0263 324/309 |
| 2013/0132054 A1* | 5/2013 | Sharma | G06F 19/12 703/9 |
| 2013/0243294 A1* | 9/2013 | Ralovich | G06T 7/0012 382/131 |
| 2014/0073915 A1* | 3/2014 | Lee | A61B 5/0261 600/425 |
| 2014/0334710 A1 | 11/2014 | Fouras et al. | |
| 2015/0324962 A1* | 11/2015 | Itu | G06T 7/00 382/130 |
| 2015/0335308 A1* | 11/2015 | Pedrizzetti | G06T 7/2066 600/454 |

OTHER PUBLICATIONS

Vasilevskiy, Alexander, and Kaleem Siddiqi. "Flux maximizing geometric flows." Pattern Analysis and Machine Intelligence, IEEE Transactions on 24.12 (2002): 1565-1578.*

Schenkel, Torsten, et al. "MRI-based CFD analysis of flow in a human left ventricle: methodology and application to a healthy heart." Annals of biomedical engineering 37.3 (2009): 503-515.*

Solem, Jan Erik, Markus Persson, and Anders Heyden. "Velocity based segmentation in phase contrast mri images." Medical Image Computing and Computer-Assisted Intervention—MICCAI 2004. Springer Berlin Heidelberg, 2004. 459-466.*

Frangi, Alejandro F., Wiro J. Niessen, and Max A. Viergever. "Three-dimensional modeling for functional analysis of cardiac images, a review."Medical Imaging, IEEE Transactions on 20.1 (2001): 2-5.*

Tresoldi, D., et al. "Mapping aortic hemodynamics using 3D cine phase contrast magnetic resonance parallel imaging: evaluation of an anisotropic diffusion filter." Magnetic Resonance in Medicine 71.4 (2014): 1621-1631.*

Sahni, Onkar, et al. "Efficient anisotropic adaptive discretization of the cardiovascular system." Computer Methods in Applied Mechanics and Engineering 195.41 (2006): 5634-5655.*

Sourbron, S. P., and David L. Buckley. "Tracer kinetic modelling in MRI: estimating perfusion and capillary permeability." Physics in medicine and biology 57.2 (2011): R1.*

Boutsianis, Evangelos, et al. "Computational simulation of intracoronary flow based on real coronary geometry." European journal of Cardio-thoracic Surgery 26.2 (2004): 248-256.*

Heys, Jeffrey J., et al. "On mass-conserving least-squares methods." SIAM Journal on Scientific Computing 28.5 (2006): 1675-1693.*

Mihalef, et al., "Model-Based Estimation of 4D Relative Pressure Map from 4D Flow MR Images", Statistical Atlases and Computational Models of the Heart, Imaging and Modeling Challenges, Lecture Notes in Computer Science, vol. 8330, 2014, pp. 236-243.

* cited by examiner

METHOD AND SYSTEM FOR BLOOD FLOW VELOCITY RECONSTRUCTION FROM MEDICAL IMAGES

This application claims the benefit of U.S. Provisional Application No. 61/873,404, filed Sep. 4, 2013, the disclosure of which is herein incorporated by reference.

BACKGROUND OF THE INVENTION

The present invention relates to blood flow velocity reconstruction from medical image, and more particularly to reconstructing a velocity field that conserves flux from medical images used to measure blood flow.

The are several available technologies, such as Phase Contrast Magnetic Resonance Imaging (PC-MRI), Cine MRI, Doppler ultrasound, and Particle Image Velocimetry, that can be used to measure flow inside of a bounded cavity, be it industrial in nature (e.g., a pipe or tank of fluid) or biological (e.g., blood flow in a blood vessel, heart, etc.). However, velocity data measured using these technologies can suffer from noise artifacts that move the velocity field out of the space of divergence free vector fields. That is, due to the noise artifacts, mass is not conserved in the measured velocity field.

Conventional techniques for velocity reconstruction from measured data essentially act as enhancement filters in order to enforce incompressibility of the given velocity field. Such filters are either global, or more commonly, have compact support given by voxel masks approximating the region of interest. However, in such conventional techniques, the reconstructed velocity is not guaranteed to conserve flux, and these techniques may not work properly for reconstructing velocity in realistic problems that may have multiple inlets or outlets.

BRIEF SUMMARY OF THE INVENTION

The present invention provides a method and system for blood flow velocity reconstruction from medical images. Embodiments of the present invention utilize inlet and outlet locations to impose appropriate boundary conditions to a projection based velocity reconstruction methodology such that the reconstructed velocity field conserves an expected flux or flux distribution through the outlets.

In one embodiment of the present invention, flow system geometry of a flow conduit is generated from medical image data, the flow system velocity including one or more inlets, walls, and one or more outlets of the flow conduit. A measured velocity field is extracted from the medical image data. Inlet and wall fluxes are estimated. Outlet fluxes are estimated such that mass conservation is constrained based on the inlet and wall fluxes. A reconstructed velocity field is calculated by solving flux-constrained Poisson (FCP) equations that are constrained by the estimated output fluxes.

These and other advantages of the invention will be apparent to those of ordinary skill in the art by reference to the following detailed description and the accompanying drawings.

DETAILED DESCRIPTION

The present invention provides a method and system for blood flow velocity reconstruction from medical images. Embodiments of the present invention are described herein to give a visual understanding of the velocity reconstruction method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

As used herein, flux refers to flow of a volume of fluid through a surface per unit time, alternatively defined as the integral of the rate of volumetric flow along the surface area. In conventional methods for velocity reconstruction from measured data there is no attempt to use any knowledge of the inlet flux or outlet flux distribution, besides the noisy velocity measurements. Due to this limiting approach, the correct output flux distribution cannot be imposed when there are multiple outlets, and such conventional methods can only work with one inlet-one outlet data. This is quite different from a pipe or vessel network, such as for example the aorta with supraaortic arteries. In contrast with embodiments of the present invention, conventional methods do not identify exact wall, inlet, or outlet locations, and therefore are limited to using Dirichlet boundary conditions either far away outside these locations or several grids inside. As a consequence, various artifacts may appear. For example, a stationary wall flux may be nonzero or the total flux is not being conserved. It can be noted that a flux erroneously measured to be approximately zero on an outlet, could still be zero after the reconstruction if the appropriate outlet flux is not enforced.

Embodiments of the present invention provide a method and system for "flux-constrained" velocity reconstruction, in which inlet and outlet locations are utilized to impose appropriate boundary conditions to the projection based velocity reconstruction methodology such that the reconstructed velocity field conserves an expected flux or flux distribution through the outlets. The results of this velocity reconstruction are beneficial, as, for example, relative pressure maps can be computed accurately from the reconstructed (physically meaningful) velocity field. Furthermore, the velocity reconstruction method provides physically meaningful velocity near the walls of a cavity, thereby providing important information with clinical value, typically missing from standard computations, such as wall shear stress and quantities associated with wall shear stress.

According to an advantageous embodiment, the flux-constrained velocity reconstruction method can be implemented by building the flow system geometry, including identified walls, inlets, and outlets, estimating velocity initial conditions, estimating inlet flux and wall flux, estimating outlet flux distribution, adjusting outlet fluxes such that mass conservation is constrained, solving a Flux-Constrained Poisson (FCP) equation, and subtracting the solution of the FCP equation from the measured velocity to obtain a new velocity field. The velocity initial conditions can use full data given throughout the computation domain, obtained for example Flow MR data, or sparse 2D PC-MRI, Doppler ultrasound, Ply, etc. The flux estimation throughout the boundary domains can also be based on different measurement modalities, for example 2D PC-MRI. Accordingly, embodiments of the present invention can use mixed modality data for the initial velocity field and boundary fields. For example, 4D Flow MR can be used to initialize the boundary flux data at any time step, and 2D Flow MR can be used to estimate the fluxes at the domain boundaries, resulting in better constraints for the fluxes. This leads to velocity reconstructed fields that are useable for further computation of relative pressure fields and wall shear stress information.

Velocity as measured using PC-MRI or other methods, is not discretely incompressible, and suffers from various aliasing and noise artifacts, especially near the walls, due for example to jumps in the density across the wall. A corrected velocity field $U^{new}$ can be defined as:

$$U^{new} = U^{measured} - \nabla \lambda, \quad (1)$$

where $U^{measured}$ is the measured velocity field and $\lambda$ is a potential function. Applying the divergence operator and requiring that the new velocity field be incompressible, results in the following Poisson's equation for the potential field:

$$\Delta \lambda = \nabla \cdot U^{measured}. \quad (2)$$

The Neumann boundary conditions compatible with Equation (1) can be obtained by projecting Equations (2) in the direction normal to the boundary:

$$\frac{\partial \lambda}{\partial n} = (U^{measured} - U^{new}) \cdot n. \quad (3)$$

Once Equations (2) and (3) are solved, we have that $\int_{\partial D} U^{new} \cdot n = 0$, which is simply the condition that the total flux through the boundaries of the domain D is conserved in the corrected velocity field. If the walls are rigid, this condition simply requires that the flow coming in through the inlets is the same as the flow leaving through the domain outlets.

It can be noted that the elliptic system of Equations (2) and (3), in principle, allows any prescribed flux $\int_A U^{new} \cdot n$ through a surface A (e.g., inlet, outlet, wall) to be used, as long as the global sum satisfies mass conservation $\Sigma_{A_i} \int_{A_i} U^{new} \cdot n = 0$, where it is assumed that the domain D is an orientable manifold and n is the unit field normal to the boundary of the domain. According to an advantageous embodiment of the present invention, such prescribed fluxes are used as constraints for the boundary velocity $U^{new}$, subject to mass conservation, and this constrained $U^{new}$ is used to specify the boundary conditions, as expressed in Equation (3). This can be formalized as the Flux-Constrained Poisson (FCP) equations:

$$\begin{cases} \Delta \lambda = \nabla \cdot U^{measured} & (4.1) \\ \frac{\partial \lambda}{\partial n} = (U^{measured} - U^B) \cdot n & (4.2) \\ \int_{A_i} U^B \cdot n = f_i & (4.3) \\ \sum_{A_i} f_i = 0 & (4.4) \end{cases}$$

Relations (4.3) and (4.4) are prescribed mass conservation equations for $U^B$, and they ensure that $$\int_{\partial D} \frac{\partial \lambda}{\partial n} = \int_{\partial D} U^{measured} \cdot n,$$

which is the necessary compatibility condition for the Poisson equation with Neumann boundary conditions expressed on Equations 4.1 and 4.2. One advantage of solving the FCP equations is that they enable the recovery of a "physically realistic velocity field". This means that even though the measured flow may be clearly wrong from the point of view of global flux conservation through the boundaries, the boundary conditions can be adjusted such that they ensure boundary flux conservation, or furthermore they satisfy fluxes measured through other (more accurate) methods. This can be very useful, for example, when one uses defective data obtained using modalities such as Flow MRI or Doppler ultrasound, where the inlet flux does not match the sum of the outlet fluxes. Similar systems that have been proposed do not impose any constraints on fluxes at the domain boundaries. As a consequence, the resulting velocity field obtained is either imposing wrong fluxes, or it is not guaranteed to conserve boundary flux, and such velocity fields introduce errors when the velocity field is subsequently used for determination of the relative pressure field. In an advantageous implementation, Equations (4) can be solved by solving the minimization problem: $\mathrm{argmin}(\|\nabla \lambda - U^{measured} + U^B\|_2^2)$, where $U^B$ is chosen to be divergence free and satisfying Equations (4.3) and (4.4).

Figure 1:
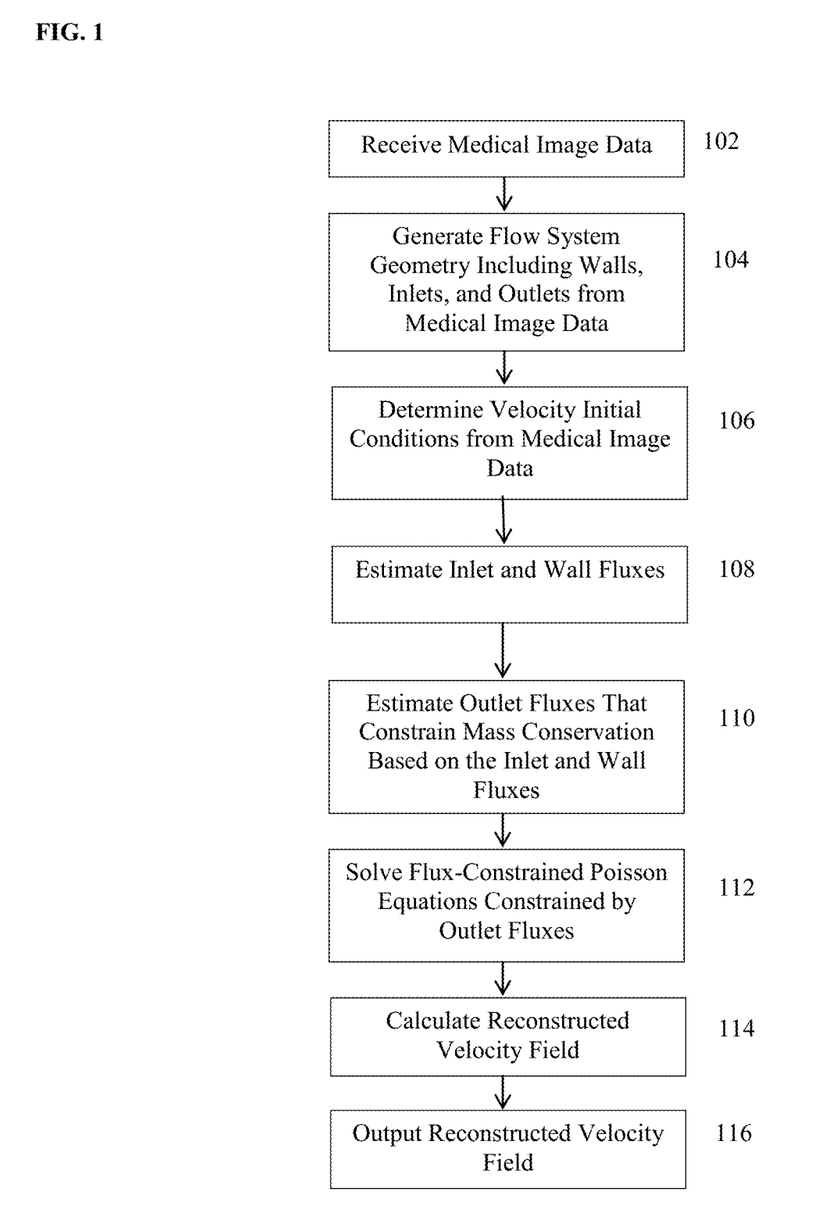
FIG. 1 illustrates a method of reconstructing a blood flow velocity field from medical images according to an embodiment of the present invention.

FIG. 1 illustrates a method of reconstructing a blood flow velocity field from medical images according to an embodiment of the present invention. The method of FIG. 1 transforms medical image data of a patient to generate a reconstructed velocity field representing the blood flow of the patient. At step 102, medical image data of a patient is received. The medical image data includes anatomical information of the patient and blood flow information of the patient. The medical image data can be acquired using any medical imaging modality, such as magnetic resonance imaging (MRI), magnetic resonance angiography (MRA), computed tomography (CT), digital subtraction angiography (DSA), ultrasound, etc. In an exemplary implementation, the medical image data can include 4D (3D+time) flow MRI images, such as 4D phase-contrast MRI (PCMRI) images. The image data may also include 2D flow MRI (e.g., PCMRI) images. The medical image data may be received directly from an image acquisition device, such as an MR scanner, and ultrasound scanner, etc., or the medical image data may be received by loading medical image data that has been previously stored, for example on a memory or storage of a computer system.

Figure 2:
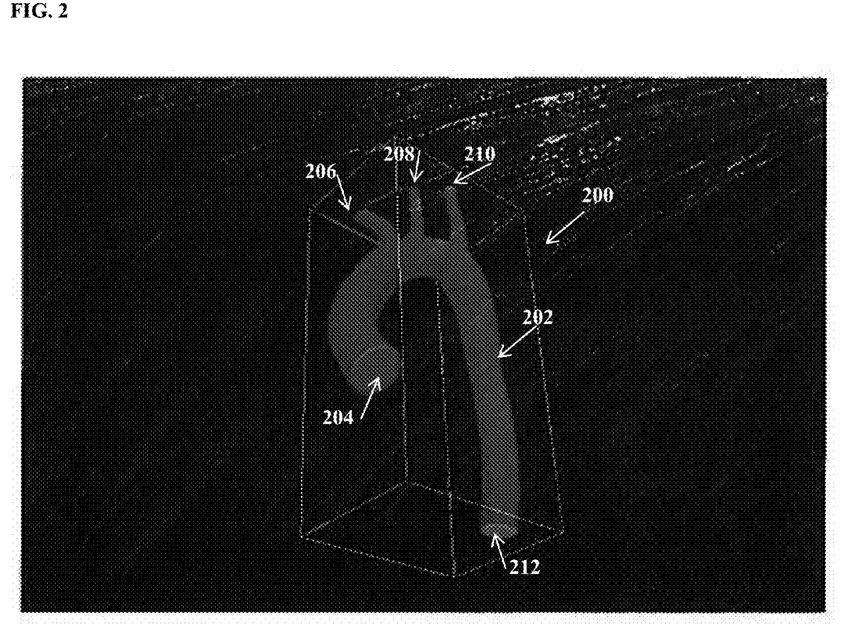
FIG. 2 illustrates an example of flow system geometry generated for the aorta.
Figure 3:
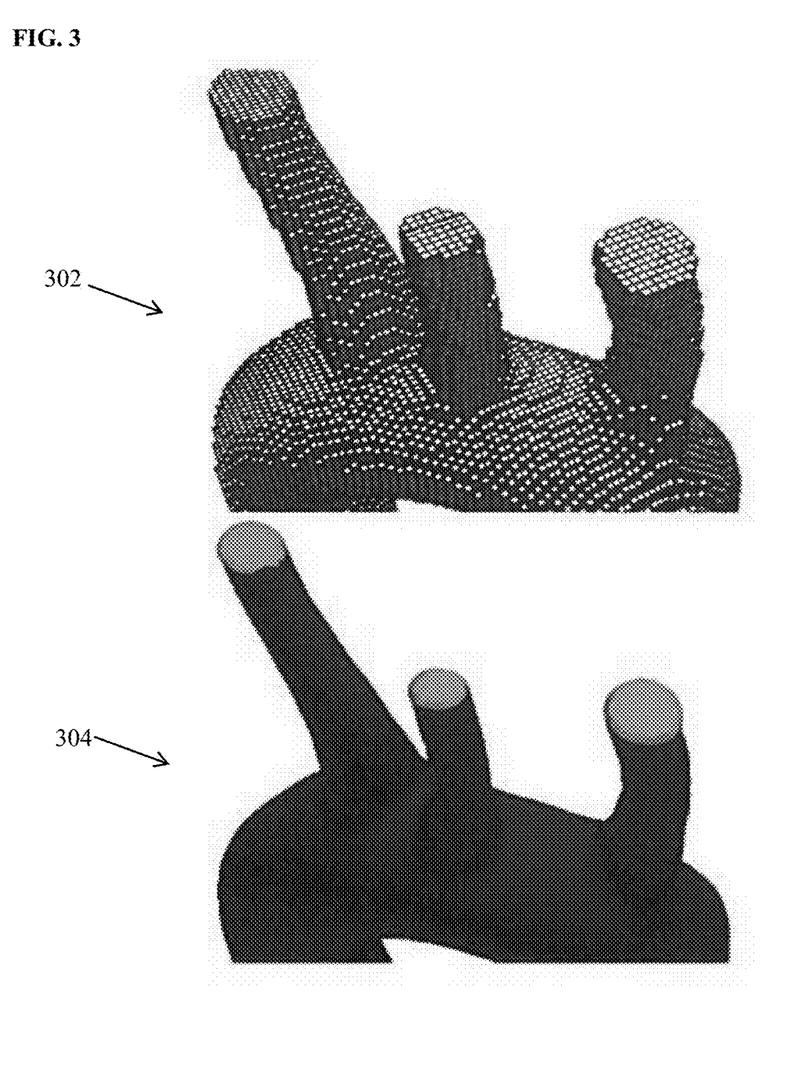
FIG. 3 shows a comparison between aortic geometry extracted using a generic voxelization approach and aortic geometry extracted by smoothing a binary mask of the aorta using a level set approach.

At step 104, flow system geometry, including the walls, inlets, and outlets, is generated from the medical image data. In particular, the image data is used to generate a binary mask that approximates the domain of the flow conduit (blood vessel, heart, etc.) This can be performed using various segmentation techniques, such as intensity thresholding on the original or filtered image data, region growing techniques, energy minimization techniques, or machine learning techniques. The regularity of the data can be increased by 3D smoothing of the binary mask or by 2D smoothing an isosurface or level set representation extracted from the binary mask. 2D or 3D Taubin smoothing or other volume-preserving smoothing technique can be used in order to ensure that the volume of the domain is preserved approximately. The vessel surface is cut into cross-sections and each cross-section is tagged/defined as an inlet, wall, or outlet. The tagging can be performed manually by a user, automatically using an automated tagging algorithm, or semi-automatically. For example, user inputs may be received to indicate the locations of inlets and outlets, and the remaining portions of the binary mask can be automatically tagged as walls. FIG. 2 illustrates an example of flow system geometry generated for the aorta. As shown in FIG. 2, a binary mask 200 of the aorta is extracted, and the wall 202, inlet 204, and outlets 206, 208, 210, and 212 of the aorta are tagged. The vessel surface is defined as a zero of a level set. FIG. 3 shows a comparison between aortic geometry 302 extracted using a generic voxelization approach and aortic geometry 304 extracted by smoothing a binary mask of the aorta using a level set approach.

Returning to FIG. 1, at step 106, velocity initial conditions are determined from the flow information in the medical image data. In particular, a measured velocity field representing the blood flow in the medical image data can be used as the initial measurement, which will then be reconstructed to remove noise and artifacts. For example, the initial velocity field over the domain of the vessel (or other blood flow conduit) can be measured directly from 4D Flow MRI (e.g., PCMRI) or 4D Ultrasound image data.

At step 108, the inlet and wall fluxes are estimated. In one embodiment, the inlet and wall fluxes can be estimated based on the velocity initial conditions. In this case, the measured velocity is used to calculate fluxes on the inlet and walls of the vessel. The flux for the inlet can be calculated by integrating velocities on a cross-section of the inlet. According to a possible implementation, multiple virtual inlet surfaces that are located in the inlet region can be used to extract multiple flux measurements in the inlet region in order to estimate and mitigate noise effects. Each flux measurement can be calculated by integrating velocities on the respective inlet surface. The maximum or median measured flux can be used to specify the inlet flux. The wall flux for rigid walls, for example for small to medium vessels other than the aorta, can be specified to be zero. For larger vessels, such as the aorta, with non-rigid walls, the wall flux can be measured by sampling the velocity at the wall, but Flow MRI wall velocities are noisy and therefore can introduce large measurement errors. According to an advantageous implementation, the wall flux for non-rigid walls can be determined using wall motion detected from intensity maps of the 4D medical image data. It is to be understood that the present invention is not limited to estimating the inlet and wall fluxes based on the initial measured velocity field, and according to other possible embodiments, the inlet and wall fluxes can be estimated based on other external measures, such as for example cardiac flow obtained from stroke volume rate of change.

At step 110, outlet fluxes are estimated that constrain mass conservation based on the inlet and wall fluxes. Blood vessel outlet flux measurements are typically marred by low quality of Flow MRI data in outlet regions, due to insufficient resolution (e.g., 1-3 pixels across) which leads to partial volume effects. Accordingly, the image data cannot be used to directly impose the measured flux values. In one embodiment, the outlet flux distribution in the measured velocity field is determined and the output fluxes are then distributed according to the distribution of the measured output fluxes, but scaled such that they add up to the total inlet+wall flux. The outlet flux distribution can be determined as a percentage of the inlet flux for each outlet. In another embodiment, biological laws of flux distribution, such as Murray's law, can be used to specify the flux distribution between the outlets. In another embodiment, 2D flow MRI (e.g., 2D PCMRI) measurements, which have higher resolution and less noise that the 4D flow MRI measurements, can be acquired at the outlet locations and used to estimate the fluxes at each outlet. This provides an outlet flux distribution, but the outlet fluxes still have to be corrected based on the inlet and wall fluxes to ensure that mass conservation is achieved. Once the outlet flux distribution is determined, the velocities on the outlet boundary cells are scaled or imposed as a profile over a cross-section of each outlet, such that they match the boundary flux conditions. The velocities of the outlets can be scaled such that the outlet fluxes maintain the determined distribution but add up to the total inlet+wall flux. The velocities for each outlet can be defined by imposing a profile, such as a flat profile, a parabolic profile, or a powerlaw profile on the cross-section of each outlet. The new velocities and their corresponding fluxes obey Equations (4.3-4.4) in the FCP equations. That is, $U^B$ is defined by the measured velocities at inlet and the wall (0 for a rigid wall) and the velocities estimated at the outlets that correspond to the outlet fluxes that are determined such that the total flux of the inlet, wall, and outlets add up to zero.

As described above, various techniques can be used to estimate the outlet flux distribution and calculate the outlet fluxes and velocities. According to an advantageous implementation, user input can be received to interactively select how the outlet flux is estimated and/or how the outlet fluxes and velocities are calculated. According to another possible embodiment, machine learning techniques can be used to calculate the outlet fluxes. For example, a machine-learning based statistical model, such as a regression model, can be trained on a database of training samples to find the outlet distribution or the estimated outlet flux values based on features, such as radius at the inlet, radius at each outlet, length of vessel, measured inlet flux, and measured wall flux.

At step 112, the flux-constrained Poisson (FCP) equations constrained by the outlet fluxes are solved. In particular, in Equations (4.3-4.4) outlet fluxes that satisfy mass conservation are estimated and used to calculate outlet velocities that are included in the boundary constraints $U^B$. The system of Equations (4.1-4.2) is now a consistent Poisson equation with Neumann boundary conditions, which can be solved using standard numerical methods, such as multigrid or pre-conditioned conjugate gradient methods. A possible level set based discretization of the equations is described in Mihalef et al., "Model-Based Estimation of 4D Relative Pressure Map from 4D Flow MR Images", Statistical Atlases and Computational Models of the Heart. Imaging and Modeling Challenges, Lecture Notes in Computer Science Volume 8330, 2014, pp 236-243, which is incorporated herein by reference.

Figure 4:
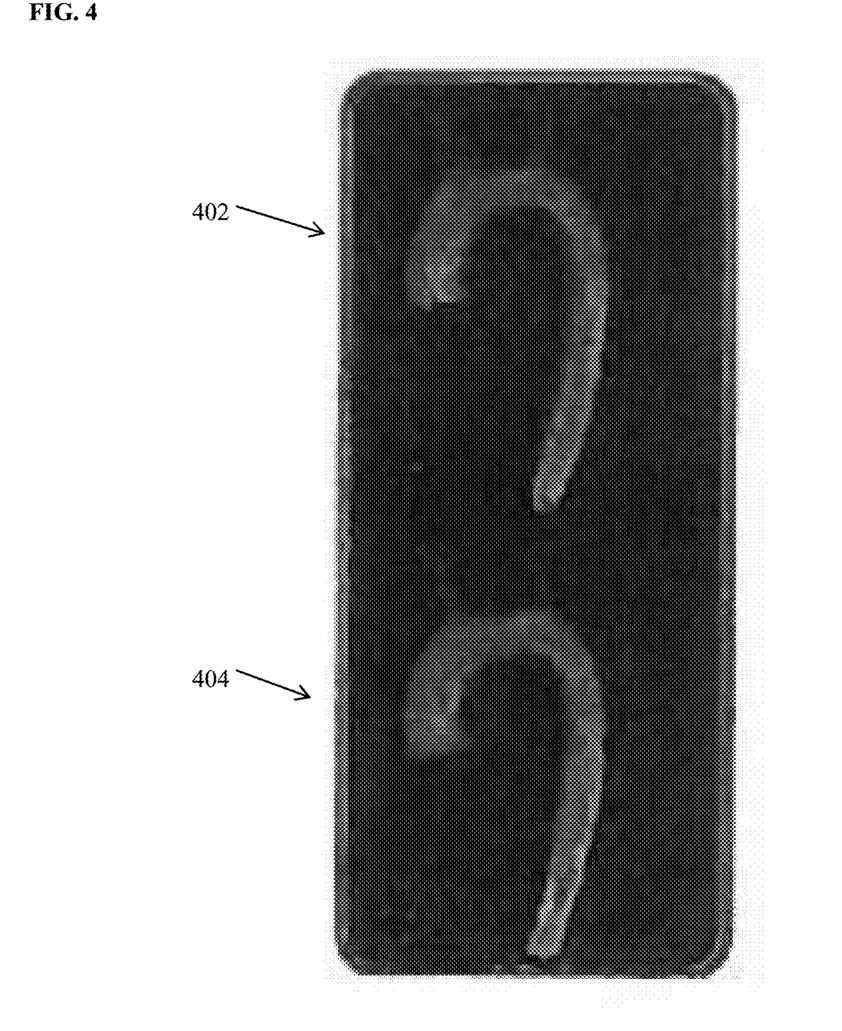
FIG. 4 illustrates exemplary results of blood flow velocity reconstruction using the method of FIG. 1.

At step 114, the reconstructed velocity field is calculated. In particular, the gradient field $\nabla$ is determined by solving the FCP equations in step 112. The reconstructed velocity field is then calculated by substituting the calculated gradient field $\nabla$ into Equation (1) to calculate $U^{new}$. At step 116, the reconstructed velocity field is output. The reconstructed velocity field can be output by displaying the reconstructed velocity field, for example on a display device of a computer system. The reconstructed velocity field can also be calculated by storing the reconstructed velocity field on a memory or storage of a computer system. The reconstructed velocity field can be used by other algorithms, for example to calculate relative pressure maps or quantities, such as wall shear stress. FIG. 4 illustrates exemplary results of blood flow velocity reconstruction using the method of FIG. 1. As shown in FIG. 4, image 402 is a measured velocity field and image 404 is a reconstructed velocity field generated from the measured velocity field.

Examples 1 and 2 are examples of problems that can occur when outlet fluxes are not used to constrain the solution for velocity reconstruction. The method of FIG. 1, which constrains the solution using the outlet fluxes corrects these issues.

Example 1

Consider uniform inviscid flow in a 2D tube of length 20 and width 2, placed lengthwise along the x axis, and between −1 and 1 along the y axis. The theoretical velocity field equals $U^B(x,y)=(1,0)$. Let us assume that the measured velocity field becomes worse as we approach the outlet (e.g., due to partial volume effects), and let us model this as $U^{measured}=(1-x,0)$. The measured divergence is therefore $\nabla \cdot U^{measured}(x,y)=-1$ and the associated Poisson equation is $\Delta\lambda=-1$. We look for solutions such that the gradient of $\lambda$ has no component in y, namely $$\frac{\partial \lambda}{\partial y} = 0.$$

This implies $\lambda_{yy}=0$ hence $\lambda_{xx}=-1$, and therefore $\lambda_x=-x+f(y)$. The reconstructed velocity is $U^{new}=U^{measured}-\nabla\lambda=(1-x+x-f(y),0)=(1,0)-(f(y),0)=U^B(x,y)-(f(y),0)$. We note that $$\int \frac{\partial \lambda}{\partial n} = -20,$$

while $\int\Delta\lambda=-40$, so the chosen Neumann boundary conditions are incompatible with the Poisson equation. On the other hand, choosing zero Dirichlet boundary conditions, as typically done, would lead to $f(y)=-10$, which gives and erroneous solution. If one attempts to use the conjugate gradient method with the above Neumann boundary conditions, we have that $$\frac{\partial \lambda}{\partial n}(0, y) = -f(y) \text{ and } \frac{\partial \lambda}{\partial n}(20, y) = -20 + f(y).$$

To make the problem solvable, one can subtract the appropriate residue difference from the right hand side, essentially solving $\Delta\lambda=-0.5$, and obtaining in the end $U^{new}=(0.5,0)$, which matches the "internal" flux of the measured velocity but is not the energy minimizer we are looking for. The FCP approached described in FIG. 1, on the other hand, provides the correct solution of $U^{new}=(1,0)$.

Example 2

Consider now the Poiseuille flow in a 2D tube of length 20 and width 2, placed lengthwise along the x axis, and between −1 and 1 along the y axis. The velocity field equals $U^B(x,y)=(1-y^2,0)$ and the pressure is $p(x,y)=40-2x$, where we considered the viscosity coefficient equal to one, and we chose for convenience the outlet (placed at x=20) to have zero pressure. Let us assume that the measured velocity becomes worse as we approach the outlet (e.g., due to partial volume effects), and let us model this as $U^{measured}=((1-x)*(1-y^2),0)$. The measured divergence is therefore $\nabla\cdot U^{measured}(x,y)=y^2-1$. The associated Poisson equation is $\Delta\lambda=y^2-1$. We look for solutions such that the gradient of $\lambda$ has no component in y, namely $$\frac{\partial \lambda}{\partial y} = 0.$$

This implies $\lambda_{yy}=0$ hence $\lambda_{xx}=y^2-1$, and therefore $\lambda_x=x(y^2-1)+f(y)$. The reconstructed velocity is $U^{new}=U^{measured}-\nabla\lambda=(1-y^2-f(y),0)=(1-y^2,0)-(f(y), 0)=U^B(x,y)-(f(y),0)$. In our specific example, we see that $$U^{new} = U^B + \frac{\partial \lambda}{\partial n}(0, y),$$

so that the reconstructed velocity depends highly on the Neumann boundary condition in the inlet. If the outlet were placed at the origin by definition, then the reconstructed velocity would depend on the Neumann boundary condition at the outlet. Accordingly, the reconstructed solution will depend in an essential way on the inlet and outlet boundary conditions chosen for the Poisson equation. In particular, setting the boundary conditions to be Dirichlet $\lambda=0$ on a boundary somewhere outside the original domain (possibly on the bounding box) does not offer any guarantees on the error introduced. In fact, for this example, by using such an approach, after imposing the boundary conditions at x=0 and x=20, we get $f(y)=-10*(1-y^2)$, which is 1000% error. In the FCP approach described in FIG. 1 on the other hand, we have $U^{measured}-U^B=(-x*(1-y^2),0)$, hence the boundary conditions imposed are $$\frac{\partial \lambda}{\partial n}(0, y) = 0 \text{ and } \frac{\partial \lambda}{\partial n}(20, y) = -20*(1 - y^2).$$

In this case we get $f(y)=0$, hence the solution is reconstructed exactly.

Figure 5:
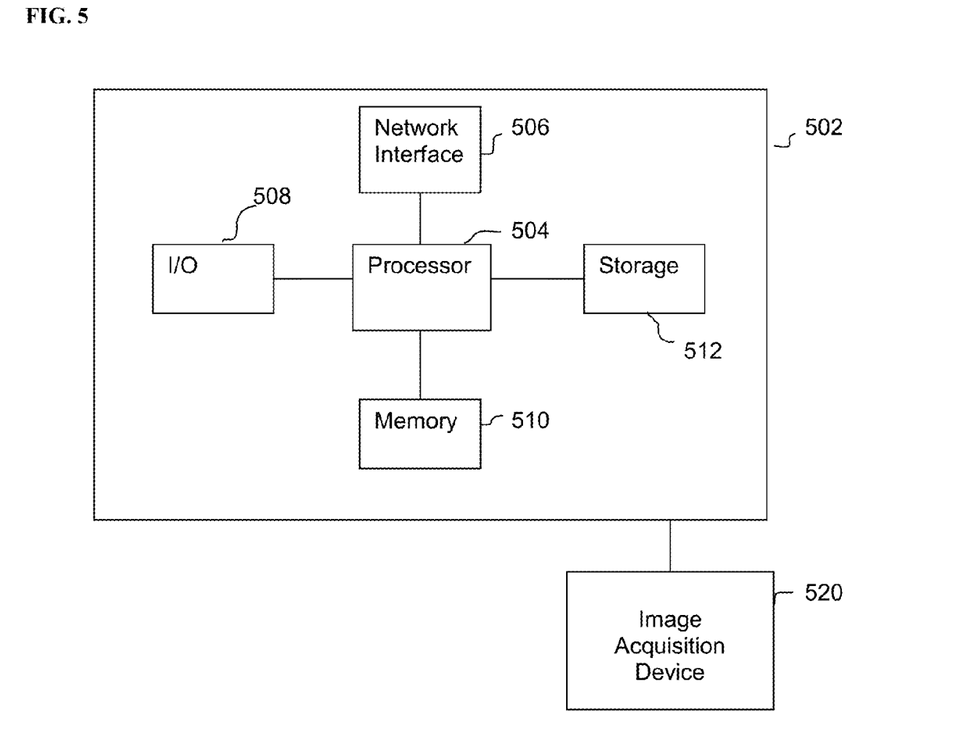
FIG. 5 is a high-level block diagram of a computer capable of implementing the present invention.

The above-described methods for blow flow velocity reconstruction can be implemented on a computer using well-known computer processors, memory units, storage devices, computer software, and other components. A high-level block diagram of such a computer is illustrated in FIG. 5. Computer 502 contains a processor 504, which controls the overall operation of the computer 502 by executing computer program instructions which define such operation. The computer program instructions may be stored in a storage device 512 (e.g., magnetic disk) and loaded into memory 510 when execution of the computer program instructions is desired. Thus, the steps of the methods of FIG. 1 may be defined by the computer program instructions stored in the memory 510 and/or storage 512 and controlled by the processor 504 executing the computer program instructions. The storage device 512 that stores the computer program instructions may be a non-transitory computer readable medium. An image acquisition device 520, such as an MRI or ultrasound image acquisition device, etc., can be connected to the computer 502 to input image data to the computer 502. It is possible to implement the image acquisition device 520 and the computer 502 as one device. It is also possible that the image acquisition device 520 and the computer 502 communicate wirelessly through a network. The computer 502 also includes one or more network interfaces 506 for communicating with other devices via a network. The computer 502 also includes other input/output devices 508 that enable user interaction with the computer 502 (e.g., display, keyboard, mouse, speakers, buttons, etc.). One skilled in the art will recognize that an implementation of an actual computer could contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for blood flow velocity reconstruction from medical image data, comprising:
    generating flow system geometry of a flow conduit from medical image data, the flow system geometry including an inlet, walls, and one or more outlets of the flow conduit;
    extracting a measured velocity field from the medical image data;
    estimating inlet and wall fluxes;
    estimating outlet fluxes such that mass conservation is constrained based on the inlet and wall fluxes; and
    calculating a reconstructed velocity field by solving flux-constrained Poisson (FCP) equations that are constrained by the estimated output fluxes.

2. The method of claim 1, wherein generating flow system geometry of a flow conduit from medical image data, the flow system geometry including an inlet, walls, and one or more outlets of the flow conduit comprises:
    segmenting a binary mask of the flow conduit in the medical image data; and
    tagging inlet, wall, and outlet regions of the binary mask.

3. The method of claim 2, wherein tagging inlet, wall, and outlet regions of the binary mask comprises:
    cutting binary mask into a plurality of cross-sections; and
    tagging each of the plurality of cross-sections as inlet, wall, or outlet.

4. The method of claim 1, wherein estimating inlet and wall fluxes comprises:
    estimating the inlet and wall fluxes based on at least one of the measured velocity field or other external velocity measures.

5. The method of claim 1, wherein estimating inlet and wall fluxes comprises:
    estimating the inlet flux based on the measured velocity field by integrating measured velocities over a cross-section of the inlet.

6. The method of claim 1, wherein estimating inlet and wall fluxes comprises:
    dividing the inlet into multiple inlet surfaces;
    estimating a plurality of flux measurements by estimating a respective flux measurement for each of the multiple inlet surfaces; and
    estimating the inlet flux as one of a maximum or a median of the plurality of flux measurements.

7. The method of claim 1, wherein estimating inlet and wall fluxes comprises:
    prescribing the inlet flux from stroke volume rate of change.

8. The method of claim 1, wherein estimating inlet and wall fluxes based on the measured velocity field comprises:
    estimating the wall flux based on wall motion detected from intensity maps of the medical image data.

9. The method of claim 1, wherein estimating inlet and wall fluxes based on the measured velocity field comprises:
    estimating the wall flux to be zero for rigid walls.

10. The method of claim 1, wherein estimating outlet fluxes such that mass conservation is constrained based on the inlet and wall fluxes comprises:
    estimating an outlet flux distribution of the one or more outlets; and
    calculating outlet fluxes based on the outlet flux distribution that have a sum equal in magnitude to a sum of the inlet and wall fluxes.

11. The method of claim 10, wherein estimating an outlet flux distribution of the one or more outlets comprises:
    estimating outlet flux distribution based on outlet fluxes estimated in the measured velocity field.

12. The method of claim 10, wherein estimating an outlet flux distribution of the one or more outlets comprises:
    estimating the outlet flux distribution using a biological law of flux distribution.

13. The method of claim 10, wherein the measured velocity field is extracted from 4D flow magnetic resonance imaging (MRI) data and estimating an outlet flux distribution of the one or more outlets comprises:
    estimating an outlet flux at each of the one or more outlets using 2D flow MRI measurements obtained at each of the one or more outlets.

14. The method of claim 10, wherein calculating outlet fluxes based on the outlet flux distribution that have a sum equal in magnitude to a sum of the inlet and wall fluxes comprises:
    scaling measured velocities at the one or more outlets such that the sum of the outlet fluxes is equal in magnitude to the sum of the inlet and wall fluxes while the estimated outlet flux distribution is maintained.

15. The method of claim 10, wherein calculating outlet fluxes based on the outlet flux distribution that have a sum equal in magnitude to a sum of the inlet and wall fluxes comprises:
    imposing velocities having one of a flat profile, a parabolic profile, or a powerlaw profile on a cross-section of each of the one or more outlets such that the outlet fluxes match the estimated outlet flux distribution and the sum of the outlet fluxes is equal in magnitude to the sum of the inlet and wall fluxes.

16. The method of claim 1, wherein calculating a reconstructed velocity field by solving flux-constrained Poisson (FCP) equations that are constrained by the estimated output fluxes comprises:
    specifying Neumann boundary conditions for velocities at the one or more outlets that impose the estimated outlet boundary conditions as constraints on the FCP equations.

17. The method of claim 1, wherein the flow conduit is a vessel.

18. The method of claim 1, wherein the flow conduit is an aorta.

19. An apparatus for blood flow velocity reconstruction from medical image data, comprising:
  means for generating flow system geometry of a flow conduit from medical image data, the flow system geometry including an inlet, walls, and one or more outlets of the flow conduit;
  means for extracting a measured velocity field from the medical image data;
  means for estimating inlet and wall fluxes;
  means for estimating outlet fluxes such that mass conservation is constrained based on the inlet and wall fluxes; and
  means for calculating a reconstructed velocity field by solving flux-constrained Poisson (FCP) equations that are constrained by the estimated output fluxes.

20. The apparatus of claim 19, wherein the means for generating flow system geometry of a flow conduit from medical image data, the flow system geometry including an inlet, walls, and one or more outlets of the flow conduit comprises:
  means for segmenting a binary mask of the flow conduit in the medical image data; and
  means for tagging inlet, wall, and outlet regions of the binary mask.

21. The apparatus of claim 19, wherein the means for estimating inlet and wall fluxes comprises:
  means for estimating the inlet and wall fluxes based on at least one of the measured velocity field or other external velocity measures.

22. The apparatus of claim 19, wherein the means for estimating outlet fluxes such that mass conservation is constrained based on the inlet and wall fluxes comprises:
  means for estimating an outlet flux distribution of the one or more outlets; and
  means for calculating outlet fluxes based on the outlet flux distribution that have a sum equal in magnitude to a sum of the inlet and wall fluxes.

23. The apparatus of claim 22, wherein the means for estimating an outlet flux distribution of the one or more outlets comprises:
  means for estimating outlet flux distribution based on outlet fluxes estimated in the measured velocity field.

24. The apparatus of claim 22, wherein means for estimating an outlet flux distribution of the one or more outlets comprises:
  means for estimating the outlet flux distribution using a biological law of flux distribution.

25. The apparatus of claim 22, wherein the measured velocity field is extracted from 4D flow magnetic resonance imaging (MRI) data and the means for estimating an outlet flux distribution of the one or more outlets comprises:
  means for estimating an outlet flux at each of the one or more outlets using 2D flow MRI measurements obtained at each of the one or more outlets.

26. A non-transitory computer readable medium storing computer program instructions for blood flow velocity reconstruction from medical image data, the computer program instructions when executed by a processor, cause the processor to perform operations comprising:
  generating flow system geometry of a flow conduit from medical image data, the flow system geometry including an inlet, walls, and one or more outlets of the flow conduit;
  extracting a measured velocity field from the medical image data;
  estimating inlet and wall fluxes;
  estimating outlet fluxes such that mass conservation is constrained based on the inlet and wall fluxes; and
  calculating a reconstructed velocity field by solving flux-constrained Poisson (FCP) equations that are constrained by the estimated output fluxes.

27. The non-transitory computer readable medium of claim 26, wherein generating flow system geometry of a flow conduit from medical image data, the flow system geometry including an inlet, walls, and one or more outlets of the flow conduit comprises:
  segmenting a binary mask of the flow conduit in the medical image data; and
  tagging inlet, wall, and outlet regions of the binary mask.

28. The non-transitory computer readable medium of claim 26, wherein estimating inlet and wall fluxes comprises:
  estimating the inlet and wall fluxes based on at least one of the measured velocity field or other external velocity measures.

29. The non-transitory computer readable medium method of claim 26, wherein estimating inlet and wall fluxes comprises:
  estimating the inlet flux based on the measured velocity field by integrating measured velocities over a cross-section of the inlet.

30. The non-transitory computer readable medium of claim 26, wherein estimating inlet and wall fluxes comprises:
  dividing the inlet into multiple inlet surfaces;
  estimating a plurality of flux measurements by estimating a respective flux measurement for each of the multiple inlet surfaces; and
  estimating the inlet flux as one of a maximum or a median of the plurality of flux measurements.

31. The non-transitory computer readable medium of claim 26, wherein estimating inlet and wall fluxes comprises:
  prescribing the inlet flux from stroke volume rate of change.

32. The non-transitory computer readable medium of claim 26, wherein estimating inlet and wall comprises:
  estimating the wall flux based on wall motion detected from intensity maps of the medical image data.

33. The non-transitory computer readable medium of claim 26, wherein estimating outlet fluxes such that mass conservation is constrained based on the inlet and wall fluxes comprises:
  estimating an outlet flux distribution of the one or more outlets; and
  calculating outlet fluxes based on the outlet flux distribution that have a sum equal in magnitude to a sum of the inlet and wall fluxes.

34. The non-transitory computer readable medium of claim 33, wherein estimating an outlet flux distribution of the one or more outlets comprises:
  estimating outlet flux distribution based on outlet fluxes estimated in the measured velocity field.

35. The non-transitory computer readable medium of claim 33, wherein estimating an outlet flux distribution of the one or more outlets comprises:
  estimating the outlet flux distribution using a biological law of flux distribution.

36. The non-transitory computer readable medium of claim 33, wherein the measured velocity field is extracted from 4D flow magnetic resonance imaging (MRI) data and estimating an outlet flux distribution of the one or more outlets comprises:
  estimating an outlet flux at each of the one or more outlets using 2D flow MRI measurements obtained at each of the one or more outlets.

37. The non-transitory computer readable medium of claim 33, wherein calculating outlet fluxes based on the outlet flux distribution that have a sum equal in magnitude to a sum of the inlet and wall fluxes comprises:

scaling measured velocities at the one or more outlets such that the sum of the outlet fluxes is equal in magnitude to the sum of the inlet and wall fluxes while the estimated outlet flux distribution is maintained.

38. The non-transitory computer readable medium of claim 33, wherein calculating outlet fluxes based on the outlet flux distribution that have a sum equal in magnitude to a sum of the inlet and wall fluxes comprises:

imposing velocities having one or a flat profile, a parabolic profile, and a powerlaw profile on a cross-section of each of the one or more outlets such that the outlet fluxes match the estimated outlet flux distribution and the sum of the outlet fluxes is equal in magnitude to the sum of the inlet and wall fluxes.

39. The non-transitory computer readable medium of claim 26, wherein calculating a reconstructed velocity field by solving flux-constrained Poisson (FCP) equations that are constrained by the estimated output fluxes comprises:

specifying Neumann boundary conditions for velocities at the one or more outlets that impose the estimated outlet boundary conditions as constraints on the FCP equations.

* * * * *